United States Patent [19]

Eichen et al.

[11] Patent Number: 4,708,653

[45] Date of Patent: * Nov. 24, 1987

[54] DENTAL DRILL BIT HAVING DISORDERED, WEAR RESISTANT BORON CARBON EXTERNAL COATING

[75] Inventors: Erwin Eichen, West Bloomfield; James Flasck, Rochester, both of Mich.

[73] Assignee: Ovonic Synthetic Materials Company, Troy, Mich.

[ * ] Notice: The portion of the term of this patent subsequent to Jun. 10, 2003 has been disclaimed.

[21] Appl. No.: 908,448

[22] Filed: Sep. 17, 1986

Related U.S. Application Data

[63] Continuation-in-part of Ser. No. 535,352, Sep. 23, 1983, abandoned.

[51] Int. Cl.$^4$ .................................................. A61C 3/02
[52] U.S. Cl. .................................... 433/165; 428/698; 433/166
[58] Field of Search ................ 433/165, 166; 428/698, 428/699

[56] References Cited

U.S. PATENT DOCUMENTS

| | | | |
|---|---|---|---|
| 3,670,416 | 6/1972 | Kroder | 433/165 X |
| 4,058,898 | 11/1977 | Nash | 433/166 |
| 4,270,903 | 6/1981 | Nash | 433/165 |
| 4,526,542 | 7/1985 | Kochis | 433/165 |
| 4,594,294 | 6/1986 | Eichen et al. | 428/457 X |

*Primary Examiner*—Nancy Swisher
*Attorney, Agent, or Firm*—Richard M. Goldman; Marvin S. Siskind

[57] ABSTRACT

A wear resistant dental burr coating is provided. The wear resistant coating comprises an external layer of disordered boron and carbon applied to the dental burr. In accordance with one embodiment, the disordered boron and carbon external coating is of a composition $B_xC_{1-x}$ where x is from about 0.60 to about 0.90.

6 Claims, 2 Drawing Figures

DENTAL DRILL BIT HAVING DISORDERED, WEAR RESISTANT BORON CARBON EXTERNAL COATING

CROSS REFERENCE TO RELATED APPLICATION

This is a continuation-in-part of our commonly assigned, copending, U.S. application Ser. No. 535,352 filed Sept. 23, 1983, now abandoned for Disordered Boron-Carbon Wear Resistant Coating and Method.

ART TO WHICH THE INVENTION RELATES

This invention relates to coatings and more particularly to coatings on surfaces that are subjected to friction or wear, and to coatings for dental drill bits.

BACKGROUND

Filling a dental cavity involves the steps of removing decayed tooth structure, e.g., with a dental hand piece and burr. After the decayed tooth structure is removed it is replaced with a filling material, e.g., gold, silver, or amalgam. The filling material is then smooth to remove rough spots and assure that the filling material matches the shape of the tooth.

The removal of decayed material and smoothing the filling both involve the use of dental drills. Dental drilling gives rise to heat and vibration, both sources of patient discomfort.

Modern dentistry is practised with the use of high speed drill bits, also known as dental burrs. These drill bits rotate at speeds of about 800,000 revolutions per minute.

A need exists for a wear resistant dental burr coating that retains its hardness at the high speeds necessary to avoid patient discomfort. Moreover, the material must be relatively non-toxic while avoiding the low lubricity and irregular topography of many refractory compounds.

SUMMARY OF THE INVENTION

In accordance with a broad aspect of the invention, a disordered boron and carbon external coating is provided atop an underlying burr substrate, the disordered boron-carbon coating exhibiting low toxicity and excellent resistance to wear.

The wear resistant coating is formed as a thin layer on the coated surface of an article such as a tool or other substrate and preferably comprises a coating of boron carbide. As used herein, "substrate" and "article" are interchangeable and include the underlying hard or elastic coating, coatings, or layer other than the external boron-carbide wear resistant coating of the invention.

Tools coated in accordance with the invention utilizing disordered boron and carbon above an underlying coating generally have excellent hardness and lubricity characteristics which result in increased lifetimes and, depending on the particular application, improved surface finishes on parts or workpieces machined therewith.

The wear resistant, disordered, boron and carbon surface coatings can be amorphous, polycrystalline (and lacking long range compositional order), microcrystalline or a mixture of any combination of those phases.

Preferably, the composition of the surface coating is:

$$x 1 B x C$$

where "B" represents boron, "C" represents carbon and "x" and "1−x" represent the relative amount of boron and carbon respectively, present in the coating, "x" being from about 0.60 to about 0.90. Disordered coatings of boron and carbon on either side of this range are also included within the scope of the invention. Most preferably, the coatings are disordered boron carbide ($B_4C$). Thus, included in accordance with the present invention are coatings which are non-stoichiometric as well as those that are stoichiometric.

The dental burr coating of the present invention is disordered when formed. It is believed that a disordered wear resistant coating performs better than a single phase crystalline coating due to diffusive bonding between the burr substrate and the boron-carbide coating, resulting in better adherence. Disordered materials also lack extended lattice planes through which fractures can propagate and in general can withstand relatively high deformation forces without fracture. Such materials are generally less susceptible to corrosion than a single phase crystalline material. It is believed that the foregoing advantages are more fully realized with an amorphous or substantially amorphous external coating.

A non-stoichiometric boron-carbide dental burr coating can be utilized in which the coating composition can be tailor-made to achieve desired characteristics while avoiding the formation of extended lattice planes which could adversely affect the adherence, wear resistance or other properties of the coating.

Any suitable method to form the disordered boron-carbide coating can be used. One method of forming the coating is by sputtering. Since sputtering can take place at a relatively low substrate temperature (generally about 200° or less, for example), the coating can be formed while avoiding significant changes in the properties of the dental burr material, thereby providing a surface that has increased resistance to wear and excellent lubricity. After a dental burr, with or without a coating, has been in use, a coating in accordance with the invention can be applied thereto, to achieve a desired tolerance or otherwise replace material that has been worn from the dental burr. Thus, the invention makes possible the reclamation of dental burr that would otherwise be discarded.

The disordered boron and carbon dental burr coating of the invention can be further characterized as being non-toxic and relatively inert and stable, with good resistance to degradation as a result of exposure to, e.g., humidity and heat.

BRIEF DESCRIPTION OF THE DRAWINGS

The invention may be understood by reference to the FIG. 1 shows a dental handpiece, including a dental burr.

DETAILED DESCRIPTION

Figure 1:
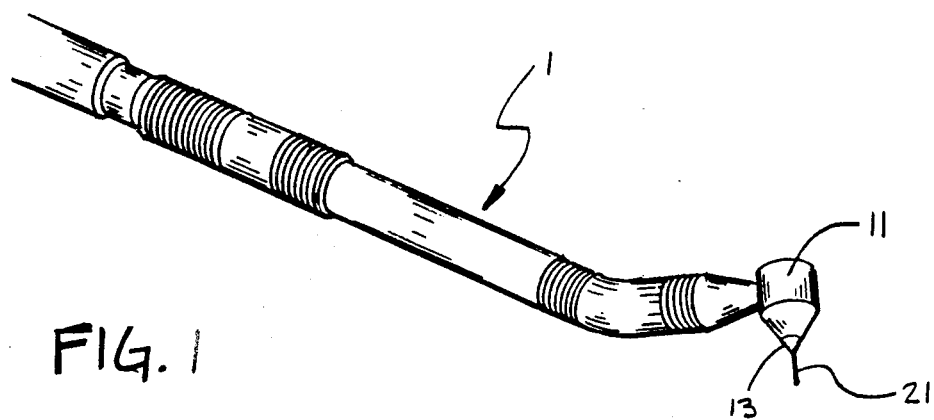

The disordered wear resistant dental burr surface coating of the invention is preferably formed by sputtering, although any suitable technique which forms a disordered coating of boron and carbon having suitable adherence to the underlying coating and physical integrity can be utilized. The preferred type of sputtering is dc magnetron sputtering with a bias voltage. Sputtering allows the coating to be applied at relatively low temperature and is less likely to affect the dental burr substrate properties than other techniques which require relatively high temperature.

While sputter depositing techniques are generally known to those skilled in the art, to maximize the benefits of the invention, it is advantageous to form the desired coating with a sputtering technique that is adapted to the particular geometry of the dental burr to be coated. Usually, a dc or rf bias is applied to the dental burr substrate during application of the coating by sputtering. The bias may improve adhesion of the coating formed on the the substrate, reduce stress in the coating and increase the density of the coating. The dental burr substrate geometry in part determines the most desirable sputtering technique for a particular application.

Prior to sputter depositing, it is important to provide an atomically clean surface on the portion of the underlying dental burr structure that is to be coated. This facilitates the formation of a uniform external boron-carbide coating which adheres to the underlying coating. There are several methods known to those skilled in the art for providing an atomically clean surface for sputtering and any such method may be utilized. The following surface preparation method is provided by way of example only and is not to be construed as a limitation upon the present invention.

In accordance with one method for providing an atomically clean surface, the dental burr is cleaned with a chlorinated hydrocarbon degreaser. Thereafter, the dental burr is rinsed in methanol and is then subjected to either plasma or dry chemical etching. When plasma etching is utilized, preferably a fluorinated carrier gas, such as carbon tetrafluoride is utilized. The carrier gas decomposes and provides fluorine which cleans the uncoated dental burr surface. The final step for providing an atomically clean surface for the coating is sputter etching in an argon plasma.

After an atomically clean surface has been provided on the dental burr or at least on that portion of the dental burr which is to be coated with the boron and carbon exterior coating, the wear resistant boron and carbon coating can be applied.

Generally, the wear resistant, boron and carbon containing coating is applied by sputtering. The preferred sputtering conditions depend on surface geometry and the type of microstructure desired. Generally, however, it is desirable for the surface of the wear resistant boron and carbon coating to be smooth, especially for many wear-related applications. The internal microstructure of the disordered wear resistant coating may be columnar or non-columnar. For some applications, a columnar surface of the wear resistant coating can be desirable.

When it is desired to produce a columnar microstructure, any type of sputtering technique known in the art which produces a columnar microstructure can be utilized. One technique for producing a columnar microstructure applies sufficient bias voltage to the substrate to cause formation of the columnar microstructure. For some coating materials and/or substrate geometries, a columnar microstructure may not be formed, even with a high bias voltage. As is known to those skilled in the art, bias sputtering is the process of maintaining a negative bias voltage on the dental burr during deposition.

By applying a bias voltage to the dental burr, the density, purity, adhesion and internal stress of the coating can be controlled. Generally, application of a bias voltage tends to increase the density, purity and adhesion and also tends to decrease the internal stress of the coating.

The bias voltage applied to a the dental burr during sputtering may be varied in a desired sequence. The preferred bias sequencing depends on the substrate geometry and the desired microstructure. For shaped burrs, e.g., those having a surface having a relatively high (about 2.0 or greater) aspect ratio (which is the ratio of the macroscopic depth to the width of a surface, e.g. the aspect ratio of a planar surface is 0 and the aspect ratio of a surface having a depression whose depth equals its width is 1), it is desirable to initially sputter the boron and carbon coating material onto the dental burr at a relatively low bias voltage (for example, about $-100$ to $-200$ volts) to insure complete coverage. Thereafter, the bias voltage is increased to a relatively high bias voltage (for example, about $-1000$ to $-2500$ volts). The biasing voltage can be gradually increased (ramp increased) or step increased. Utilizing such bias voltage tends to promote a more dense, purer coating having greater adhesion to the underlying layer, less internal stress and also tends to promote columnar growth. It is believed that a columnar microstructure generally results in better adherence, possibly as a result of mechanical anchoring to the underlying layers.

For surfaces having an aspect ratio of about 0.5 to about 2.0, the layers are preferably sputtered at essentially a constant bias voltage, generally between $-500$ and $-1000$ volts. A higher voltage can be used. For the exterior layer, the bias voltage should be adjusted such that a relatively smooth surface is provided, if this is desired.

For surfaces having relatively low aspect ratios (between 0 and about 0.5), preferably the bias voltage initially is higher (about $-1000$ to $-2500$ volts) and can be decreased to low voltage (about $-100$ to $-200$ volts) in either step or ramp fashion, or eliminated. Again, the decrease or elimination of bias voltage usually applies towards the end of the deposition of the coating. Decreasing or relatively low bias voltage also tends to promote a relatively smooth surface which generally results in a more lubricious surface, which can be desirable in many cases.

Since sputtering can take place at relatively low substrate temperatures (generally about 200° C. or less, for example), the coatings can be formed while avoiding significant changes in the properties of the underlying burr material while providing a surface that has increased resistance to wear and excellent lubricity. Sputtering at low substrate temperatures also allows formation of the coatings in a disordered state.

To produce sputtered disordered coatings, generally the sputtering will take place at dental burr surface temperatures of less than about 200° C. and usually at about 100 ° C. or even less, to facilitate formation of disordered coatings. Thus, the coatings in accordance with the present invention can be formed at relatively low temperatures. The target generally is also cooled to prevent evaporation, melting or other unwanted degradation of the target. As a result, the coating is applied to a dental burr surface, for example, without significantly altering physical properties of the dental burr, such as the dimensions, hardness and transverse rupture strength. Generally, substrate temperatures, target compositions, deposition rates and gas pressures which tend to prevent the formation of disordered coatings should be avoided.

It is usually desirable to form a wear resistant coating that is between about one (1) and about eight (8) micrometers in thickness, with a thickness of about 2.5 micrometers usually being a good thickness for use on tools. Coatings having a thickness in excess of about eight (8) micrometers may not be particularly desirable in applications where high tolerance must be maintained since the geometry and/or size of the burr may be altered. The sputtering technique can be chosen in accordance with the guidelines hereinafter set forth relating to relatively simple and complex substrate surface geometries.

A dental hand piece 1 is shown in FIG. 1. The dental hand piece 1 includes a head 11, with a liquid outlet 13 and a dental burr 21.

Figure 2:
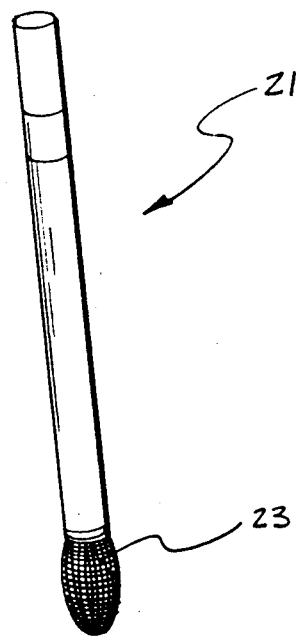
FIG. 2 shows a burr.

The dental burr 21 is shown in FIG. 2. As there shown, it includes a roughened coated portion 23 for a brading delayed tooth material or excess filling material.

It is to be understood that the coatings and methods described herein can be utilized on dental burrs that have been subjected to use, either with or without the coatings described herein. For example, after a dental burr having a coating in accordance with the invention has been in use, and is either worn or outside of a desired tolerance range, the coating in accordance with the invention can be applied to the dental burr, resulting in an increased life at the high speeds contemplated. Also, a coating can be applied to dental burrs which did not previously have a coating of the invention thereon. Thus, dental burrs which would otherwise be discarded can be reclaimed.

Generally, the hardness of the boron carbide coatings in accordance with the present invention is about KHN (50 grams)=4,700 kg/mm$^2$ as measured on a 50 micron thick (boron carbide) coating that was substantially amorphous with some microcrystalline material. Since the disordered coatings are generally relatively thin, direct measurement of a typically used thickness is impractical. It is expected that thinner coatings would have about the same hardness. However, in addition to being relatively hard, the coatings of the present invention generally also exhibit excellent lubricity. As a result, tools in accordance with the present invention have increased life and the use of such tools can result in an improved surface finish on parts machined therewith.

While this invention has been described in relation to its preferred embodiments, it is to be understood that various modifications thereof will be apparent to those of ordinary skill in the art upon reading this specification and it is intended to cover all such modifications as fall within the scope of the appended claims.

We claim:

1. A coated dental burr adapted for high speed use comprising:
    (a) a dental burr substrate;
    (b) a coating on said substrate comprising an external layer of disordered boron and carbon.

2. The coated dental burr of claim 1 wherein the layer has composition on an atomic basis of $B_1C_{1-x}$ where x is from about 0.60 to about 0.90.

3. The coated dental burr of claim 2 wherein the disordered boron and carbon comprises amorphous material.

4. The coated dental burr of claim 2 wherein the disordered boron and carbon comprises polycrystalline material.

5. The coated dental burr of claim 2 wherein the disordered boron and carbon comprises microcrystalline material.

6. The coated dental burr of claim 2 adapted for use at a speed of at least 800,000 revolutions per minute.

* * * * *